(12) United States Patent
Hakim

(10) Patent No.: US 10,201,628 B1
(45) Date of Patent: Feb. 12, 2019

(54) AIR FRESHENER

(71) Applicant: Abraham J. Hakim, Aventura, FL (US)

(72) Inventor: Abraham J. Hakim, Aventura, FL (US)

( * ) Notice: Subject to any disclaimer, the term of this patent is extended or adjusted under 35 U.S.C. 154(b) by 0 days.

(21) Appl. No.: 14/468,197

(22) Filed: Aug. 25, 2014

Related U.S. Application Data

(63) Continuation-in-part of application No. 29/478,001, filed on Dec. 30, 2013, now Pat. No. Des. 712,022, which is a continuation of application No. 29/430,549, filed on Aug. 27, 2012, now Pat. No. Des. 697,603, which is a continuation-in-part of application No. 29/392,520, filed on May 23, 2011, now Pat. No. Des. 667,100.

(51) Int. Cl.
*A61L 9/12* (2006.01)
*A61L 9/03* (2006.01)

(52) U.S. Cl.
CPC ...................... *A61L 9/12* (2013.01)

(58) Field of Classification Search
CPC .. A61L 9/03; A61L 2209/12; A61L 2209/133; A61L 9/12
USPC ........................................................ 239/34
See application file for complete search history.

(56) References Cited

U.S. PATENT DOCUMENTS

| | | | | |
|---|---|---|---|---|
| 3,400,890 A | * | 9/1968 | Gould | A41G 1/006 239/36 |
| 4,802,626 A | * | 2/1989 | Forbes | A01M 1/02 239/36 |
| 4,874,129 A | * | 10/1989 | DiSapio | A61L 9/12 239/36 |
| 4,940,272 A | * | 7/1990 | Weick | A61L 9/12 239/289 |
| 5,004,138 A | * | 4/1991 | Gabas | A61L 9/12 224/312 |
| 5,113,554 A | * | 5/1992 | Gallo | A47G 25/485 223/88 |
| 5,170,938 A | * | 12/1992 | Dewing | A47K 10/32 239/34 |
| 5,282,571 A | * | 2/1994 | Smith | A61L 9/12 239/34 |
| 8,460,609 B1 | * | 6/2013 | Wheatley | A61L 9/042 422/120 |
| 2007/0075159 A1 | * | 4/2007 | Lin | A61L 9/12 239/60 |

\* cited by examiner

*Primary Examiner* — Chee-Chong Lee
(74) *Attorney, Agent, or Firm* — Goldberg Cohen LLP

(57) ABSTRACT

An improved air freshener for mounting to an air vent grille, such as the vent of an automobile. The air freshener includes at least an upper leg and a lower leg. At least one of those legs preferably includes a flexible comb structure extending from the leg toward the louver of the air conditioner vent.

3 Claims, 6 Drawing Sheets

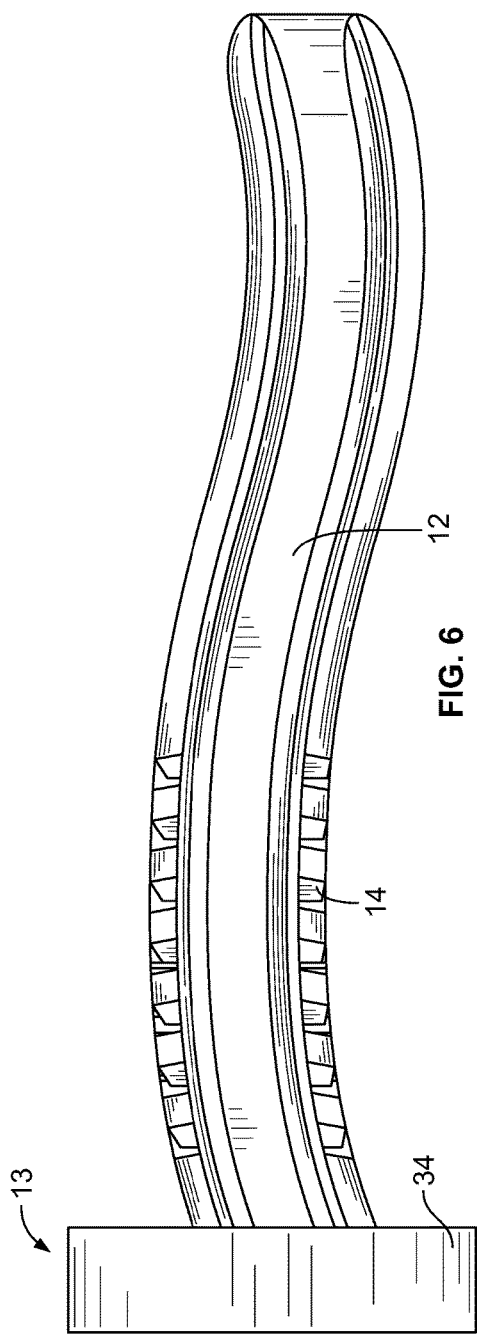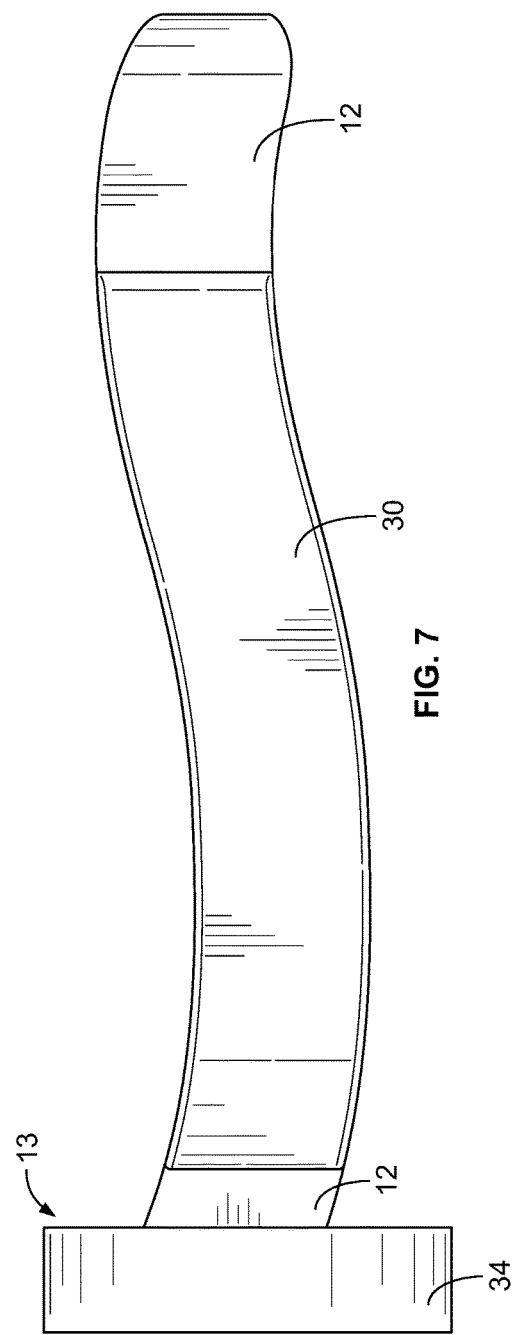

AIR FRESHENER

CROSS-REFERENCE TO RELATED APPLICATIONS

The present application is a continuation-in-part of U.S. patent application Ser. No. 29/478,001 filed Dec. 30, 2013 (pending), which is a continuation of U.S. patent application Ser. No. 29/430,549 filed Aug. 27, 2012 (patented—U.S. Pat. No. D697,603), which is a continuation-in-part of U.S. patent application Ser. No. 29/392,520 filed May 23, 2011 (patented—U.S. Pat. No. D667,100). The priority of these prior applications is claimed, and the contents thereof are fully incorporated herein by reference.

BACKGROUND OF THE INVENTION

Air fresheners for use inside a vehicle have been popular for decades. More recently, vehicle air fresheners have been adapted for installation in the grille of the vehicle's discharge air vent, as shown and described in, e.g., U.S. Pat. Nos. 5,269,723, 6,264,887, 7,687,037 and U.S. Patent Application No. US 2011/0110823. Air fresheners that are mounted to the louvers of a vehicle's air vent are generally more effective at freshening the air inside the vehicle, as the vehicle's heating or air conditioning acts as a propellant for transporting and dispersing the air freshener's odiferous particulates throughout the interior of the vehicle. Typically, vehicle vent fresheners comprise a pair of legs that extend into the air vent while straddling one of the grille's louvers, thereby mounting the air freshener to the grille.

A common drawback of the vehicle vent air fresheners on the market is the tendency for the air freshener to move about on the louver when air is blowing through the vent or when the car is in motion, or to dislodge entirely from the grille due to insecure mounting, resulting in a lost or damaged air freshener, as well as general annoyance for the occupants of the vehicle. For purposes of convenience, aesthetics, and safety, there is therefore a need for an improved vehicle vent air freshener that mounts securely in the grille of the air vent.

SUMMARY OF THE INVENTION

In accordance with the present inventions, vent air fresheners are provided that more securely mounts to, and is less likely to dislodge from, a vent.

Further in accordance with the present inventions, vent air fresheners are provided with greater surface area exposure of the Fragrance Impregnating Material (FIM).

Yet further in accordance with the present inventions, vent air fresheners are provided that use a minimal amount of non-fragrant structural elements without compromising the structural integrity of the air freshener.

It should be appreciated by one skilled in the art that the present inventions can be easily adapted to fit any number of ventilation mechanisms (such as a heater, fan, or air conditioner) having a grille, whether in the home, office, vehicle, or so forth. It should also be apparent that the air freshener of the present inventions need not be mounted in a vent or ventilation mechanism for operation. The invention can freshen the air in any relatively enclosed environment regardless of where it is mounted or whether it is mounted at all. Further advantages and benefits of the present inventions are presented below in the detailed description of the invention.

BRIEF DESCRIPTION OF THE DRAWINGS

The details of the present inventions will be made clearer by reference to the attached drawings, which show a particular embodiment of the present invention, and wherein:

FIG. 6 is a top view of the embodiment in FIG. 1;
FIG. 7 is a bottom view of the embodiment in FIG. 1.

DETAILED DESCRIPTION OF THE DRAWINGS

A preferred embodiment of air freshener 10 is shown in the figures, and comprises two odiferous components and a structural component. The structural component provides structural integrity to the air freshener and can be made of any suitably rigid and resilient material. In a preferred embodiment, the structural component is made of a plastic material, such as polypropylene, polyethylene vinyl, or the like. In a yet further preferred embodiment the structural component is made from Acetal (POM) Copolymer, such as that sold under the YUNCON® brand. Of course, the structural component need not be plastic, and other suitable materials known in the art such as wood or metal may be substituted.

In a preferred embodiment, the odiferous components comprise a fragrance impregnated material ("FIM"). The FIM can be made of a flexible gel-like material capable of maintaining a fixed shape, such as polyvinyl chloride polymer beads that are impregnated with a fragrance. Such FIM's are commonly known in the art, and are designed to gradually release fragrance into the surrounding air over time. Typically, the rate of fragrance release by the FIM is inversely proportional to the lifetime of the air freshener. Many of today's FIM's have lifetimes that span days, weeks, or even months. FIM's such as these also can be dyed during their manufacture to exhibit a color commonly associated with the fragrance being emitted. For example, a strawberry scented FIM can be dyed red. The FIM can alternatively be opaque, transparent, or translucent.

Figure 5:
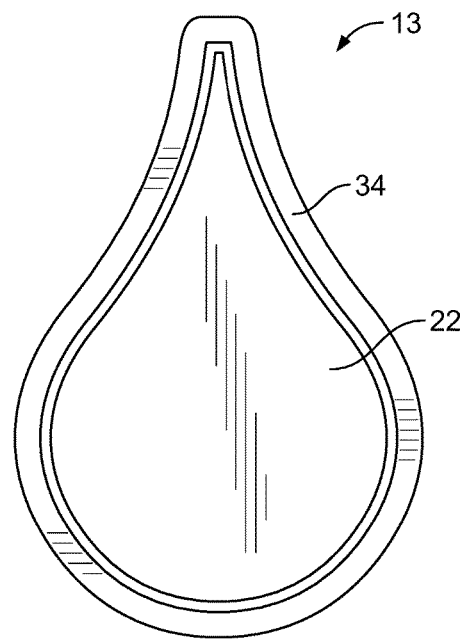
FIG. 5 is a front view of the embodiment in FIG. 1.

Now with particular reference to the figures, in a preferred embodiment of the present invention, air freshener 10 comprises lower leg 9, upper leg 11, and face 13. In one preferred embodiment, the air freshener 10 has a longer upper leg 11 and a shorter lower leg 9, one or both legs being affixed to a face 13. Alternatively, lower leg 9 and upper leg 11 can be the same length, or lower leg 9 can be longer than upper leg 11. In one preferred embodiment, the air freshener measures approximately 2.28" long, with the lower leg 9 measuring approximately 1.54" long and 0.28" wide, the upper leg 11 measuring approximately 2.12" long and 0.28" wide, and the face 13 (as shown in FIG. 5) measuring approximately 0.86" high and approximately 0.60" at its widest point. Alternately, the dimensions of the air freshener can be varied as desired.

Lower leg 9 consists of a structural aspect 16 made of a relatively rigid material, and an FIM aspect 30. FIM aspect 30 is secured to structural aspect 16 through any suitable means known in the art. In a preferred embodiment, FIM aspect 30 is secured to structural aspect 16 via a frictional fit. For example, protrusion 32 extending upward from FIM aspect 30 frictionally couples to a corresponding notch in structural aspect 16. Other securing loci can also be provided. For example, one or more protrusions extending from the bottom of structural aspect 16 can mate with corresponding notches or indentations in the top of FIM aspect 30; or vice versa, protrusions from the FIM aspect 30 can mate with notches or indentations in structural aspect 16.

Figure 1:
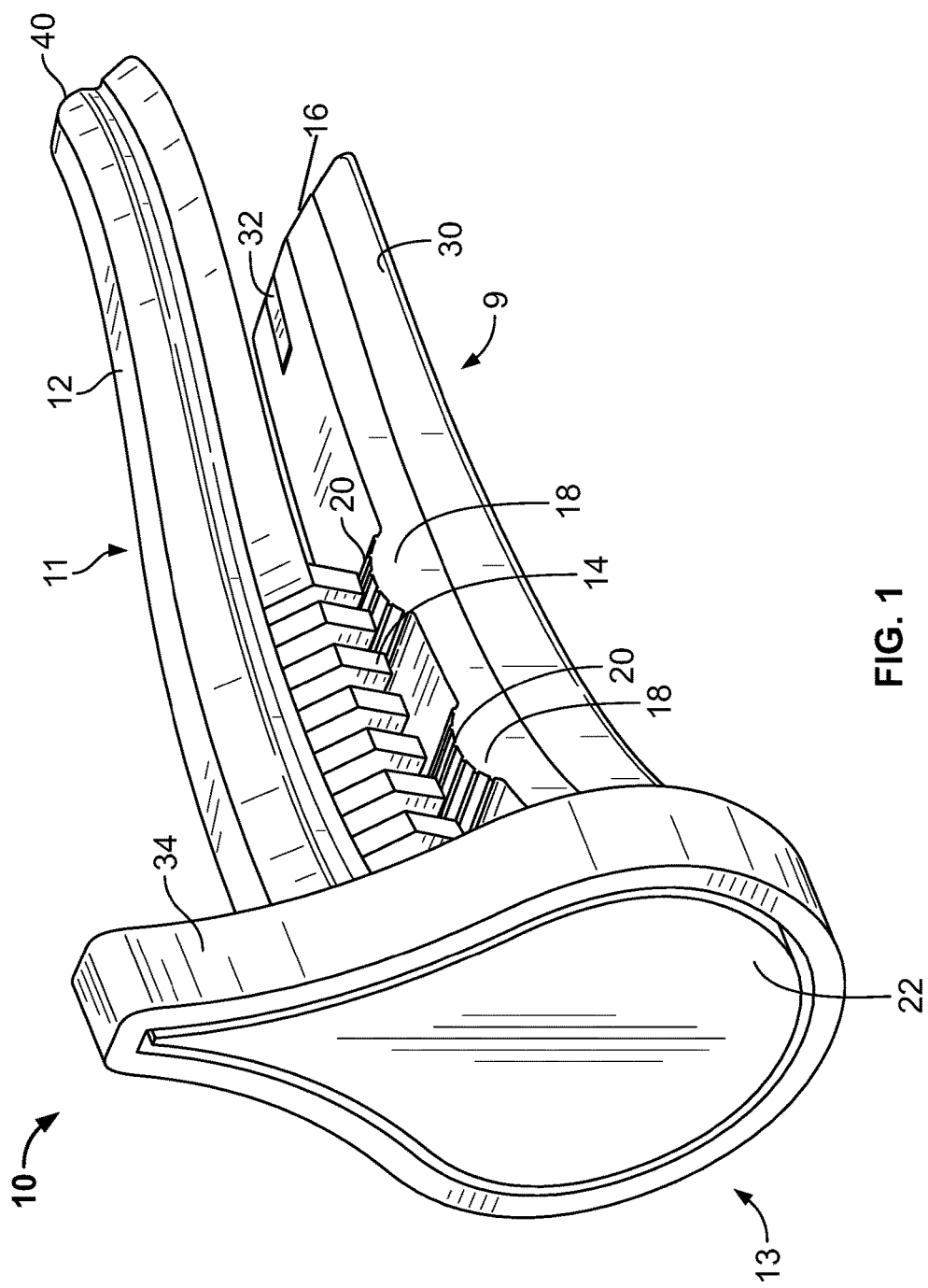
FIG. 1 is a perspective view of a preferred embodiment of the present invention.

Structural aspect 16 can also consist of one or more humps 18 extending from the top of structural aspect 16. An example of a shape for the humps is shown in FIG. 1, although humps can be provided or greater or lesser slope than those shown, and/or can be provided with one or more flat or planar surfaces, or so forth. Alternatively or additionally, humps 18 can be molded with ribs 20 on the upper surface of humps 18. It should be noted, however, that the air freshener of the present inventions can be practiced without ribs protruding from the humps 18, and likewise without any humps (or ribs) at all.

Upper leg 11 includes one or more portions made of FIM. In a preferred embodiment, upper leg 11 is made entirely of FIM, and consists of an upper portion 12 and one or more projections. Preferably, the projections are one or more fins 14 which extend downward from upper portion 12. In a preferred embodiment, the bottom of fins 14 extend below the bottom surface of upper portion 12. The fins 14 are preferably (but not necessarily) flexible. Further preferably, the fins collectively form a comb-structure, with empty space between each pair of fins, as shown in the figures. The fins can be any of numerous shapes, whether the shape shown in the figures or otherwise. For example, the fins can be tooth-like, angular, rounded, squared, or so forth. Likewise, a single uniform size and shape can be provided for all of the fins, or the group of fins can be made up of fins of multiple sizes and/or shapes.

The fins 14 are situated above humps 18, such that when air freshener 10 is mounted to an air vent, fins 14 contact the top of an air vent louver, while the one or more humps 18 contact the bottom of the same louver, thereby creating a very secure mounting of the air freshener to the air vent in which the fins 14 of the upper leg 11 and the humps 18 of the lower leg 9 effectively straddle an air vent louver. Ribs 20 situated on humps 18 help grip the louver. In addition, the collective comb structure of the downwardly extending fins 14 is also used to secure the air freshener 10 to an air vent louver. Alternatively, in place of the fins, a series of humps can be provided which extend downward towards the upper extending humps 18.

Figure 2:
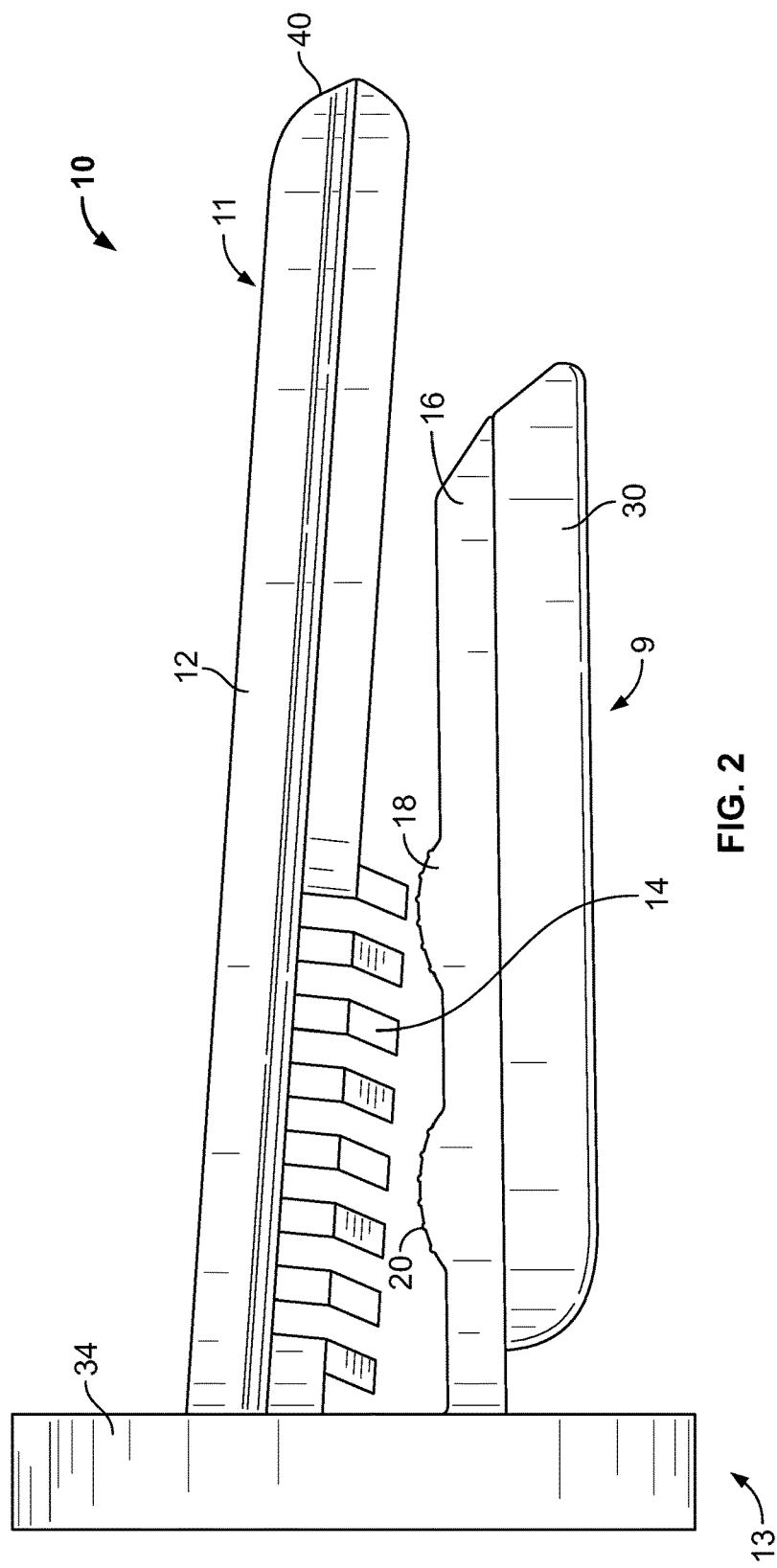
FIG. 2 is a right side view of the embodiment in FIG. 1.
Figure 3:
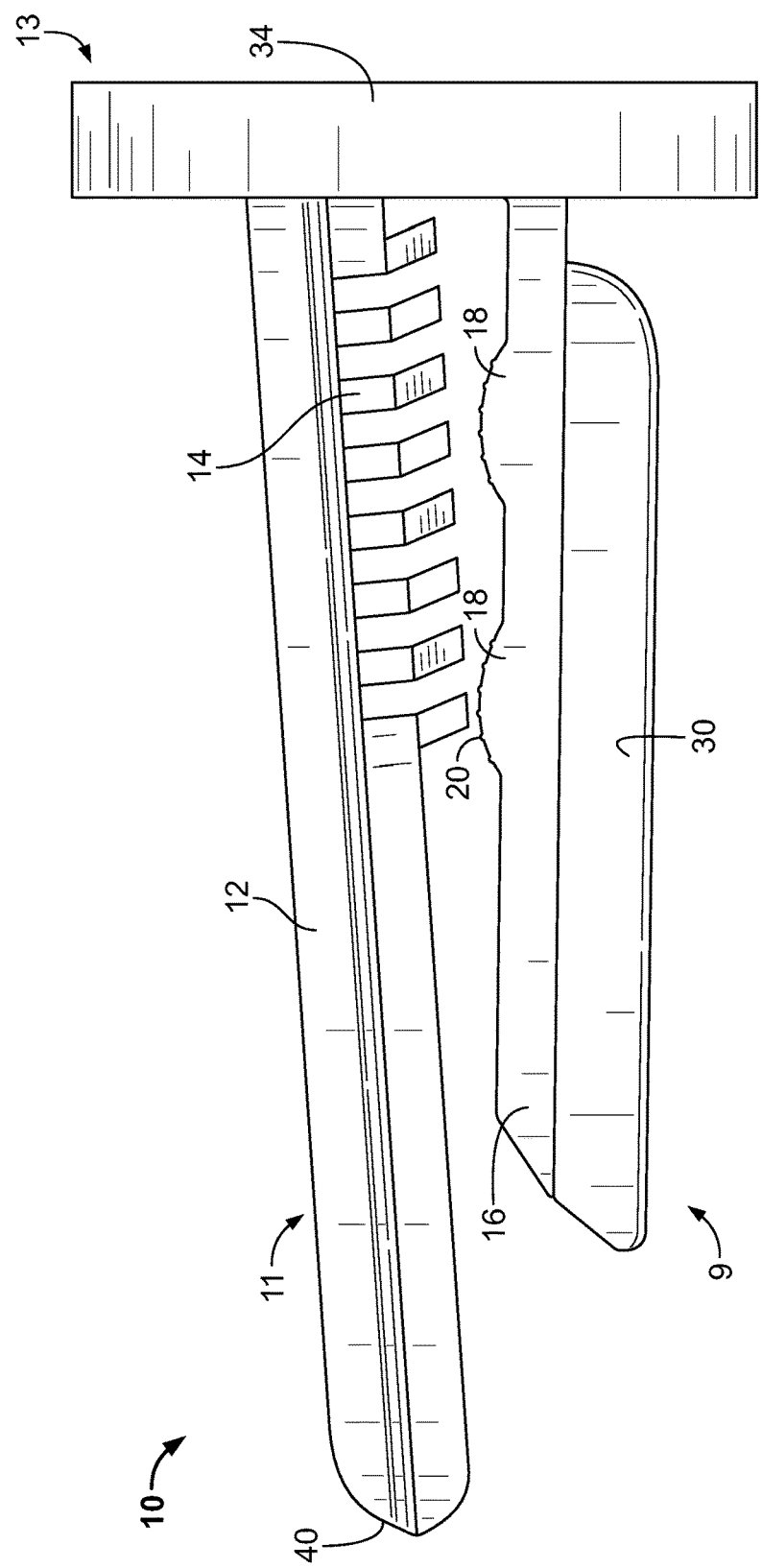
FIG. 3 is a left side view of the embodiment in FIG. 1.
Figure 4:
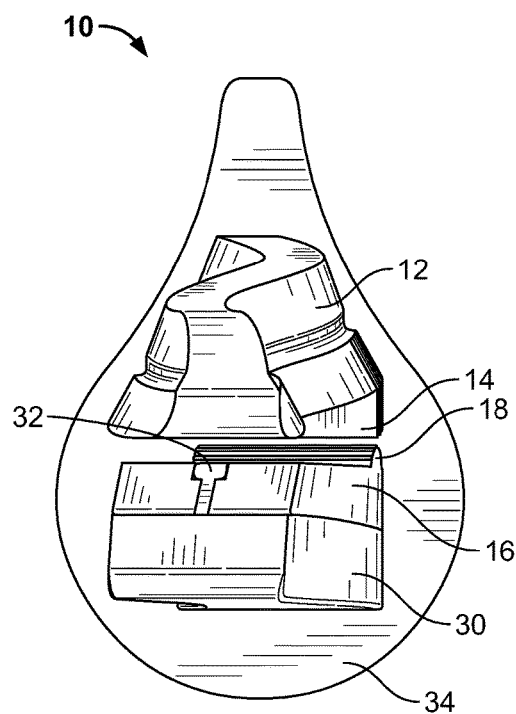
FIG. 4 is a back view of the embodiment in FIG. 1.
Figure 8:
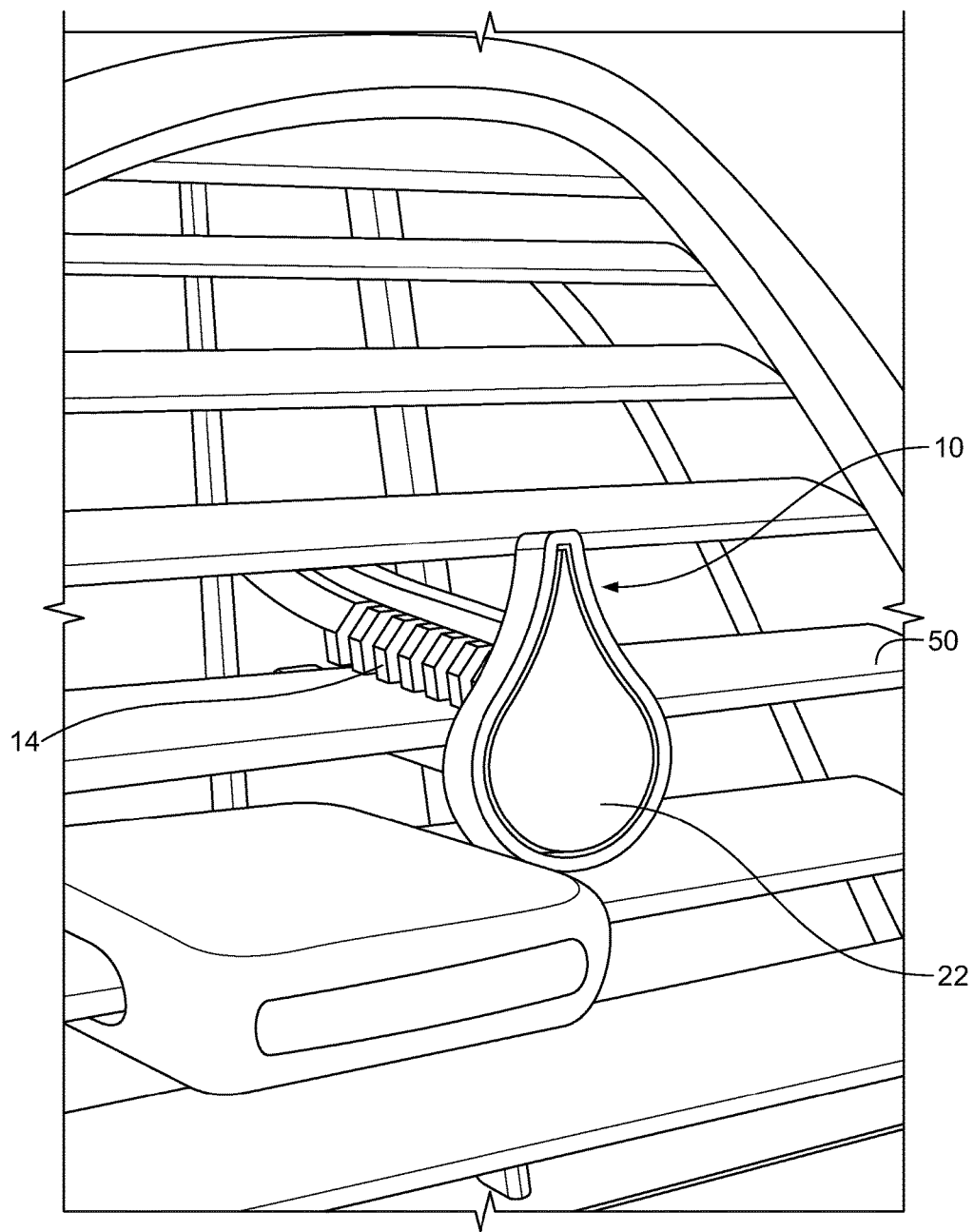
FIG. 8 is a front perspective view of the embodiment of FIG. 1 mounted to a vehicle air vent.

In a preferred embodiment, upper leg 11 slants down toward distal end 40 when the air freshener 10 is not in use (i.e. when the air freshener is not mounted—see, e.g., FIGS. 2-3). In this preferred embodiment, the lower leg 9 and upper leg 11 are biased toward each other around the louver. In practice, as shown in FIG. 8, due to the flexibility of the FIM, when the air freshener 10 is mounted about an air vent louver 50, the fins 14 and humps (not shown) securely sandwich the louver 50, applying force to the louver 50 from above and below, thereby creating a strong frictional fit between the air freshener and the louver.

As shown in the figures, a face 13 is provided to air freshener 10. In one embodiment, a droplet shape is provided for face 13, as illustrated in the figures. However, the present invention is not limited to a droplet shape, as any desired shape can be provided for the face. Similarly, the shapes of the other components of the present air freshener are provided for illustration purposes and may each likewise be varied consistent with the present inventions.

Face 13 of air freshener 10 preferably consists of an FIM aspect 22 and a structural aspect 34. In a preferred embodiment, structural aspect 34 of face 13 and structural aspect 16 of lower leg 9 are molded together as a single, monolithic structure. Alternatively, structural aspect 34 and structural aspect 16 can be molded separately and secured to each other through any suitable means known in the art. Structural aspect 16 extends distally from the back of structural aspect 34 (see, e.g., FIG. 2).

Similarly, in a preferred embodiment, FIM aspect 22 of face 13 and upper leg 11 are molded together as a single monolithic FIM component of air freshener 10. In this way FIM aspect 22 and upper leg 11 together form the first FIM component of air freshener 10 mentioned above, with the FIM aspect 30 of the lower leg 9 constituting the second FIM component of the air freshener 10. Alternatively, FIM aspect 22 and upper leg 11 can be molded separately and secured to each other through any suitable means known in the art.

In a preferred embodiment of the air freshener 10, FIM aspect 22 of face 13 is housed in, and surrounded by, the rim of structural aspect 34 of face 13, with the upper leg 11 extending through an opening (not shown) in the back of structural aspect 34 in face 13. In a further preferred embodiment, the opening in the back of structural aspect 34 is sized and shaped to provide a secure, frictional fit between the upper leg 11 and FIM aspect 22 on the one hand, and the structural aspect 34 of face 13 on the other hand. After the structural component and FIM components are molded separately, they can be assembled by hand or by any other suitable manufacturing technique known in the art, securing the FIM aspect 30 to structural aspect 16 in lower leg 9, and inserting upper leg 11 through the opening in the back of structural aspect 34 of face 13.

The legs 9, 11 of the air freshener 10 can both be straight or curved (or one can be straight and the other curved). In a preferred embodiment, the legs 9, 11 are "S"-shaped for aesthetic purposes. Moreover, a logo or other brand identification can be engraved or otherwise disposed on FIM aspect 22 of face 13 for prominent display to the user while the air freshener 10 is in use.

In addition to the improved mounting means provided by the air freshener of the present invention, it should also be appreciated that the preferred embodiments provide a high quantity of FIM surface area exposure to the air, thereby providing improved air freshening capacity, particularly when air from the ventilation system passes over the FIM, such as when the fan, air conditioner, or heater is on. Furthermore, the preferred embodiments of the present inventions provide for a very high ratio of FIM material to structural material for improved air freshening characteristics.

The above description and drawings are considered that of the preferred embodiments of the present inventions only. Modifications of the invention, including but not limited to modification to the shape, size, materials, and configuration of materials relative to one other, will occur to those skilled in the art and to those who make or use the invention. For example (not to be construed as a limiting example), the fins 14 and/or upper leg 11 and/or face 13 need not be made of FIM at all, but can instead contribute to the structural integrity of the device or be directed to some other non-air freshening purpose as an alternative to the preferred embodiments of the present invention. As a further non-limiting example, the lower leg 9 need not have humps 18 and/or ribs 20 and/or can be made entirely of FIM as an alternative to the preferred embodiments of the present invention. As a further non-limiting example, the fins (or comb-shaped structure) can extend upward from the upper surface of the lower leg toward the lower surface of the upper leg as further alternative to the preferred embodiments of the present invention. Therefore it is understood that the embodiments shown in the drawings and described herein are merely for illustrative purposes only and are not intended to limit the scope of the invention.

The invention claimed is:

1. An air freshener comprising a face, an upper leg, and a lower leg, said face further comprising a structural aspect extending outward of said upper and lower legs; said face further comprising a FIN (Fragrance Impregnating Material) aspect secured to said structural aspect;
   said upper leg comprising an upper surface, a lower surface, and a plurality of fins;
   said lower leg comprising an upper surface and a lower surface;
   wherein said upper leg and said lower leg extend from said face;
   wherein said plurality of fins extend from said lower surface of said upper leg toward said upper surface of said lower leg; and
   wherein said lower leg further comprises at least one hump protruding from said upper surface of said lower leg toward said lower surface of said upper leg; each of said at least one hump comprises at least one rib; said lower leg further comprises a plurality of discrete projections.

2. An air freshener as in claim 1, wherein said upper leg comprises a proximal end adjacent said face, and a distal end, and wherein said upper leg slants downward from said proximal end to said distal end.

3. An air freshener as in claim 2, wherein said plurality of fins is directly above said at least one hump.

* * * * *